United States Patent [19]

Takiguchi et al.

[11] 4,321,363
[45] Mar. 23, 1982

[54] ADSORBENT FOR UROKINASE CONTAINING AGAROSE

[75] Inventors: Daigaku Takiguchi, Tokyo; Eiji Itou, Odawara; Hiroaki Nakamura, Kawasaki; Izumi Kumita, Kanagawa, all of Japan

[73] Assignee: Nippon Soda Company Limited, Tokyo, Japan

[21] Appl. No.: 123,307

[22] Filed: Feb. 21, 1980

[51] Int. Cl.³ .............................................. C07H 5/06
[52] U.S. Cl. ..................... 536/18; 435/215; 536/1; 536/22; 536/24; 548/161; 548/222; 548/306
[58] Field of Search ..................... 536/1, 18, 22, 24; 548/161, 222, 306

[56] References Cited

U.S. PATENT DOCUMENTS

| | | | |
|---|---|---|---|
| 3,849,431 | 11/1974 | Gallay et al. | 548/222 |
| 4,025,622 | 5/1977 | Ogura et al. | 536/22 |
| 4,109,078 | 8/1978 | Vorbruggen et al. | 536/22 |
| 4,143,097 | 3/1979 | Fischer et al. | 548/161 |
| 4,195,128 | 3/1980 | Hildebrand et al. | 536/1 |

*Primary Examiner*—Johnnie R. Brown
*Attorney, Agent, or Firm*—George B. Oujevolk

[57] ABSTRACT

Highly pure urokinase can be produced by affinity chromatography on a novel adsorbent which comprises a water insoluble carrier and a ligand united to the carrier. The ligand is shown by the general formula

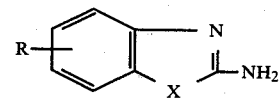

wherein X is oxygen, sulfur or imino group, and R is amino or carboxyl group.

2 Claims, No Drawings

ADSORBENT FOR UROKINASE CONTAINING AGAROSE

DETAILED DESCRIPTION OF THE INVENTION:

This invention relates to a novel adsorbent for urokinase and a process for the purification of urokinase by affinity chromatography on the adsorbent.

Urokinase is a plasminogen-activating enzyme found in trace amount in human urine and is used as an effective thrombolytic agent and a drug used together with anticancer. High purity urokinase is required because these drugs are used by an intraveneous injection.

Recently, affinity chromatography has been used as a method for the purification of human urokinase. For Example, some adsorbents having aminobenzamidine or aminobenzquanidine as a ligand are known for the purification of urokinase by affinity chromatography (Biochimica et Biophysica Acta 445, 215, 1976; U.S.P. 3,746,622).

The inventors studied the purification of urokinase of affinity chromatography and found a novel adsorbent having a completely different ligand from the known ones.

The adsorbent comprises a water insoluble carrier and a ligand of the general formula [I]

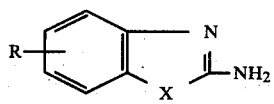

wherein X is oxygen, sulfur or imino group and R is amino or carboxyl group.

As the compound shown by the general formula [I], for example, the following compounds are given:
2,5-diaminobenzimidazole m.p. 221°~225.5° C.
2,5-diaminobenzthiazole m.p. 175° C.
2,6-diaminobenzoxazole m.p. higher than 295° C.
2-aminobenzimidazole-5-carboxylic acid The most preferable ligand is 2,5-diaminobenzimidazole.

As the spacer, for example, one of the following compounds or the combination of two or more of them is used.
$NH_2(CH_2)_nCOOH$
$NH_2(CH_2)_nNH_2$
$COOHCH_2CH_2NH_2$
$COOHCH_2CH_2COOH$ wherein n is usually an integer of 3 to 10, preferably 6.

The one end of the spacer is amino group by which the spacer is coupled to the carrier. The other end of the spacer is carboxyl group when R of the formula [I] is amino group, or amino group when R is carboxyl group. The reaction between the amino group and the carboxyl group connects the ligand to the carrier through the spacer.

The most preferable spacer is the combination of the last two, namely, $NH_2(CH_2)_nNHCOCH_2CH_2COOH$.

As the water insoluble carrier, any material having functional group to which the terminal amino group of the spacer can be coupled may be used. Suitable carriers are polysaccharides such as agarose, crosslinked dextran, celluloses and agar-agars, polymer such as acrylamide, and glass powder. Agarose is the most preferable carrier.

The ligand may be coupled to the carrier without the spacer, however, the ligand is usually coupled to the carrier by the spacer.

The adsorbent of the invention can be constructed by known processes. For example, when the carrier is agarose, first, the agarose is activated with cyanogen bromide and sequently coupled to diaminoalkane and then succinic anhydride. The affinity ligand precurser, the compound of formula [I], is then coupled to the modified agarose in the presence of water soluble carbodiimides to form the adsorbent of the invention.

In the case that the carrier is carboxymethylcellulose, it is coupled to diaminoalkanes by the reaction in the presence of water soluble carbodiimides. Then the adsorbent is constructed as same as above. Similar method is disclosed in the literature, "Method in Enzymology 34 451–455 (1974)".

The ligand may be coupled to the spacer by the substituent R of the formula [I] or by the 2-amino group when R is amino. However, the most part of the ligand is coupled to the spacer by the substituent R.

When carring out the process for the purification of urokinase, crude urokinase solution, for example, human urine or partly purified human urine is contacted with the adsorbent of the invention. For example, crude urokinase solution is made to flow through the column packed with the adsorbent to make to adsorb urokinase to the adsorbent. The adsorbed urokinase is eluted with a pertinent eluting solution after washing the column sufficiently to remove impurities.

Though the pH value of the crude urokinase solution is not critical to adsorb urokinase specifically, neutral or weak alkaline condition is preferable. Usually, crude urokinase solution is prepared so as to make a salt concentration of the solution between 0.03 and 2 M preferably 0.05 to 0.5 M, the pH of the solution is adjusted to pH 5.5–10, preferably 6–8.5 with a pertinent buffer solution, and then the solution is contacted with the adsorbent. The washing solution is an aqueous solution of inorganic salt such as sodium chloride. The concentration of the inorganic salt is in the range of from 0.03 to 2 M, preferably from 0.05 to 0.5 M. The eluting solution may be water or aqueous solution of inorganic salt such as sodium chloride, ammonium sulfate, which of pH is adjusted to 3.5–5.5, preferably 4–5. Suitable eluting solution is water or the aqueous solution of sodium chloride adjusted to the above pH with a pertinent buffer solution such as acetate buffer, the concentration of sodium chloride usually being the same as that of the washing solution or lower than that. It is preferably 0.5 M or lower, more preferably 0.3 M or lower. Highly pure urokinase is obtained from the eluate in the usual method, for example, by ultrafiltration and lyophilization.

Since the adsorbent of the invention adsorbs urkinase specifically, crude urokinase can be easily purified by affinity chromatography on the adsorbent of the invention. In addition, pyrogen can be easily removed by the process of the invention.

Further, the inventors have accomplished more preferable process for the purification of urokinase. That is the combination of hydrophobic chromatography and affinity chromatography of this invention.

The hydrophobic chromatography is carried out on a protein adsorbent having a ligand shown by the general formula

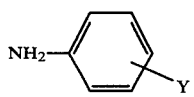

wherein Y is lower alkoxycarbonyl, lower alkylamino or quaternary ammonium substituted with alkyl.

The protein adsorbent may be produced the same as the adsorbent for urokinase of this invention. Preferable spacer is the compound of the formula $NH_2(CH_2)_nCOOH$, wherein n is preferably 5.

Crude urokinase solution is passed through the column packed with the protein adsorbent and the effluent therefrom is applied to the affinity column of the invention. Since the protein adsorbent adsorbs impurities which are difficult to remove by the affinity chromatography, high purity urokinase can be efficiently obtained by the process of the combination. The combination is particularly useful for the removal of pyrogen.

To further illustrate this invention, and not by way of limitation, the following Examples are given.

EXAMPLE 1.

To a suspension of 10 ml of AH-Sepharose 4B (Product by Farmacia Fine Chemicals: agarose-hexamethylene diamine) in 10 ml of water was added 1 g of succinic anhydride and the reaction was allowed to proceed at 4° C., maintaining the pH at 6 by adding aqueous NaOH. After the change of the pH stopped, the reaction was further continued for 5 hours. The reaction mixture was filtered and washed with 1 l of water to obtain the modified sepharose, succinyl AH-Sepharose. To a suspension of the resulting succinyl AH-Sepharose in 10 ml of water were added 60 mg of 2,5-diaminobenzimidazole hydrochloride and the pH was adjusted to 4.7 by 1 N-HCl or 1 N-NaOH. To the mixture were added 570 mg of 1-ethyl -3-(3-dimethylaminopropyl) carbodiimide hydrochloride dissolved in 1 ml of water in 5 minutes and the reaction was allowed to proceed at room temperature (20° C.) for 20 hours. The reaction product was filtered and washed successively with 0.01 N—HCl, 0.01 N—NaOH, 1 M—NaCl, 0.1 M-acetate buffer, 1 M—NaCl, Tris-buffer (pH 8.0) and then 1 M—NaCl to obtain the adsorbent of the invention having 2,5-diaminobenzimidazole as a ligand.

EXAMPLE 2.

The adsorbent of the invention having 2,5-diaminobenzthiazole as a ligand was obtained in the same way as in Example 1, using 60 mg of 2,5-diaminobenzthiazole hydrochloride instead of 2,5-diaminobenzimidazole hydrochloride.

EXAMPLE 3.

Through a column (diameter: 5 mm) packed with 1 ml of the adsorbent obtained in Example 1 was made to flow 4 ml of crude urokinase solution (2,000 international units of urokinase, specific activity of 5,000 international units/mg protein) which was prepared from human urine using Celite as a adsorbent. The column was washed with 8 ml of 0.3 M—NaCl in 0.1 M phosphate buffer (pH 7.5) and then the adsorbed urokinase was eluted with 0.4 M—NaCl in 0.1 M actate buffer (pH 4.0). The eluate contained 1,400 international units of urokinase (total protein: 33 μg). Pyrogen test according to the Japanese pharmacopeia was negative at a dosage of 8,000 international units/kg.

EXAMPLE 4.

The crude urokinase was purified in the same way as in Example 3, using the adsorbent obtained in Example 2, and 1,150 international units of urokinase (total protein: 27 μg) was obtained. Pyrogen test according to the Japanese Pharmacopeia was negative at a dosage of 8,000 international units/kg.

EXAMPLE 5.

A column (column A) of 9.2 cm diameter packed with 10 ml of the protein adsorbent wherein the groups of the formula

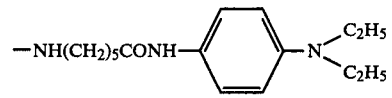

were united to Sepharose 4B (Product by Pharmacia Fine Chemicals: agarose), was connected with another column (column B) of 9.2 cm diameter packed with 10 ml of the adsorbent for urokinase obtained in Example 1.

Through the column A was passed a crude urokinase solution which was prepared by dissolving crude urokinase ($1.0 \times 10^6$ international units with a specific activity of 5,000 international units/mg protein) in 50 ml of 0.3 M—NaCl in 0.1 M phosphate buffer (pH 7.0). The column A was washed with 0.3 M—NaCl in 0.1 M phosphate buffer (pH 7.0). The effluent from the column A was successively made to flow through the column B. Then, the column A was removed and the column B was washed with 1 M—NaCl in phosphate buffer (pH 6.0). The urokinase adsorbed by the column B was eluted with 0.1 M acetate buffer (pH 4.75). The fraction containing urokinase was dialyzed and lyophilized to obtain $0.78 \times 10^6$ international units of urokinase with a specific activity of 95,200 international units/mg protein. Pyrogen test was negative at a dosage of 8,000 international units/kg.

EXAMPLE 6.

The same crude urokinase was purified in the same way as in Example 5, using the protein adsorbent (column A) wherein the groups of the formula

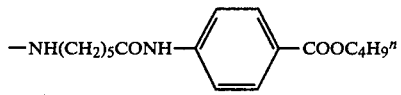

were united to Sepharose 4B. $0.76 \times 10^6$ international units of urokinase was obtained with a specific activity of 105,000 international units/mg protein. Pyrogen test was negative at a dosage of 30,000 international units/kg.

We claim:

1. An adsorbent for urokinase consisting of a carrier, a spacer and a ligand wherein the carrier is agarose, the spacer is $NH_2(CH_2)_6NHCOCH_2CH_2COOH$ and the ligand is 2,5-diaminobenzthiazole.

2. An adsorbent for urokinase consisting of a carrier, a spacer and a ligand wherein the carrier is agarose, the spacer is $NH_2(CH_2)_6NHCOCH_2CH_2COOH$ and the ligand is 2,5-diaminobenzimidazole.

* * * * *